United States Patent
Unni et al.

(10) Patent No.: US 10,881,345 B2
(45) Date of Patent: Jan. 5, 2021

(54) METHOD AND SYSTEM FOR ESTIMATION OF STRESS OF A PERSON USING PHOTOPLETHYSMOGRAPHY

(71) Applicant: Tata Consultancy Services Limited, Mumbai (IN)

(72) Inventors: Midhun Parakkal Unni, Bangalore (IN); Srinivasan Jayaraman, Bangalore (IN); Balamuralidhar Purushothaman, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 287 days.

(21) Appl. No.: 15/611,953

(22) Filed: Jun. 2, 2017

(65) Prior Publication Data
US 2017/0360351 A1  Dec. 21, 2017

(30) Foreign Application Priority Data
Jun. 3, 2016 (IN) .............................. 201621019097

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0205* (2013.01); *A61B 5/4884* (2013.01);
(Continued)

(58) Field of Classification Search
CPC ..... A61B 5/165; A61B 5/4884; A61B 5/0205; A61B 5/6898; A61B 5/725; A61B 5/7267;
(Continued)

(56) References Cited

U.S. PATENT DOCUMENTS

2007/0203416 A1 * 8/2007 Lowe ................. A61B 5/02233
600/485
2012/0022843 A1 * 1/2012 Ionasec ................... G06T 13/20
703/9
(Continued)

FOREIGN PATENT DOCUMENTS

| EP | 1440653 B1 * | 1/2008 | ......... A61B 5/02416 |
| EP | 1704817 B1 * | 3/2010 | ......... A61B 5/14551 |
| JP | 10-71137 | 3/1998 | |

OTHER PUBLICATIONS

Mona F. Taher et al., Baroreceptor Responses Derived From a Fundamental Concept, Annals of Biomedical Engineering. vol. 16, pp. 429-443, 1988 (Year: 1988).*
(Continued)

*Primary Examiner* — Omar F Fernandez Rivas
*Assistant Examiner* — Michael Edward Cocchi
(74) *Attorney, Agent, or Firm* — Finnegan, Henderson, Farabow, Garrett & Dunner LLP

(57) ABSTRACT

A system and method for determining a stress level of a person is provided. The system creates a numerical solution to mathematical model of a blood pressure (BP) regulation, lumped mathematical model of a radial artery and partial differential equation (PDE) model of the radial artery. These models are then used to generate an inference engine using the mathematical model of blood pressure (BP) regulation, the lumped mathematical model of the radial artery and the PDE model of the radial artery. The inference engine is trained using an artificial neural network technique. At the same time the PPG signal of the person is sensed and preprocessed. The preprocessed PPG signal is then given to the trained inference engine. The trained inference engine generates a stress parameter corresponding to the person based on the processed PPG signal.

11 Claims, 5 Drawing Sheets

(51) Int. Cl.
  *A61B 5/0205* (2006.01)
  *G06N 3/08* (2006.01)
  *A61B 5/021* (2006.01)
  *A61B 5/024* (2006.01)
  *G16H 50/50* (2018.01)
  *G06F 19/00* (2018.01)

(52) U.S. Cl.
  CPC ............ *A61B 5/6898* (2013.01); *A61B 5/725* (2013.01); *A61B 5/7267* (2013.01); *A61B 5/7278* (2013.01); *G06F 19/00* (2013.01); *G06N 3/08* (2013.01); *G16H 50/50* (2018.01); *A61B 5/021* (2013.01); *A61B 5/02416* (2013.01); *A61B 5/02438* (2013.01)

(58) Field of Classification Search
  CPC ... A61B 5/7278; A61B 5/021; A61B 5/02416; A61B 5/02438; G06F 19/00; G16H 50/50; G16H 50/30; G06N 3/08
  See application file for complete search history.

(56) References Cited

U.S. PATENT DOCUMENTS

| | | |
|---|---|---|
| 2013/0225950 A1 | 8/2013 | Van Elswijk et al. |
| 2013/0267796 A1* | 10/2013 | Enric Monte Moreno .................. A61B 5/021 600/301 |
| 2014/0051941 A1* | 2/2014 | Messerschmidt .. A61B 5/02416 600/301 |

OTHER PUBLICATIONS

Daniel A. Beard et al., A computational analysis of the long-term regulation of arterial pressure, F1000Research 2013, Latest published: Dec. 6, 2013, pp. 1-31 (Year: 2013).*

Elgendi, M. (Feb. 2012). "On the Analysis of Fingertip Photoplethysmogram Signals," *Current Cardiology Review*, vol. 8; pp. 14-25.

* cited by examiner

METHOD AND SYSTEM FOR ESTIMATION OF STRESS OF A PERSON USING PHOTOPLETHYSMOGRAPHY

CROSS-REFERENCE TO RELATED APPLICATIONS AND PRIORITY

The present application claims priority from Indian non-provisional specification no. 201621019097 filed on 3 Jun. 2016, the complete disclosure of which, in its entirety is herein incorporated by references.

TECHNICAL FIELD

The present application generally relates to the field of stress estimation in a person. More particularly, but not specifically, the invention provides a system and method for estimating stress of the person using the photoplethysmograph signal captured from the person.

BACKGROUND

Stress could be thought of as a catalyst which accentuates a set of chemical reactions in our body. The exact way in which stress acts is unknown although there are a set of compelling evidence that suggests that stress acts through the HPA Axes of our body to indirectly control the autonomic response. The exact mechanism of action is still being studied. The term stress is coined by Hans selye as is used today. The stress is defined as a nonspecific response of the body to any demand of change. On the other hand a stressor is the stimulus to which stress is the response. There is yet another description of stress which makes use of the fact that it is the flight or fight response offered against a threat by the human physiology. The autonomic nervous system invariably gets activated in a normal human being faced with the threat. This is complimented by the hypothalamic-pituitary-adrenal axis in releasing cortisol and a set of other hormones. The accurate and timely measurement of the stress of the person is extremely important to monitor the health of the person.

Current stress estimation methodologies make use of the Electroencephalography (EEG), Photoplethysmograph (PPG), or Electrocardiogram (ECG) signals and their derived parameters. PPG is the most commonly used technology for stress estimation. PPG indicates a signal corresponding to the quantity of light reflected from a selected part of a human body after being irradiated by light having a particular wavelength emitted from a light source of a light emitting device. Technology using PPG has been mainly developed for the purpose of determining a patient's physiological condition in association with an arterial system but usually used as an auxiliary means for diagnosing particular diseases.

These methods are neither personalizable nor takes into account different physiological systems affecting the response. For example the rennin angiotensin system, fluid structure interactions affect the how stress response gets reflected in the PPG signal. These methods also do not take into account how subject variability may be affecting the physiological response. In addition to that these methods doesn't give a quantitative estimate of stress which could be used to compare the stress estimate between people and within the same person Various other methods and systems have also been designed to provide accurate stress measurement of the person using PPG signal. None of the methods and devices provides an efficient and effective way determine stress of the person.

SUMMARY

Before the present methods, systems, and hardware enablement are described, it is to be understood that this invention is not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention which will be limited only by the appended claims.

The present application provides a system for determining a stress level of a person in real time. The system comprises a PPG Sensor, a preprocessor, a memory and a processor. The PPG sensor senses a photo-plethysmograph (PPG) signal of a person. The preprocessor preprocess the PPG signal to generate a processed PPG signal. The processor is in communication with the memory. The processor performs the steps of: create a numerical solution to mathematical model of a blood pressure (BP) regulation, create a numerical solution to lumped mathematical model of a radial artery, create a numerical solution to partial differential equation (PDE) model of the radial artery, generate an inference engine using the mathematical model of blood pressure (BP) regulation, the lumped mathematical model of the radial artery and the PDE model of the radial artery, trains the inference engine using an artificial neural network technique. The training results in a trained inference engine. And finally generates a stress parameter by the trained inference engine based on the processed PPG signal.

The present application also provides a method for estimating the stress level of the person. Initially a numerical solution to mathematical model of a blood pressure (BP) regulation is created by the processor. A numerical solution to a lumped mathematical model of a radial artery is created by the processor. A numerical solution to a partial differential equation (PDE) model of the radial artery is created by the processor. In the next step, an inference engine is generated by the processor using the mathematical model of blood pressure (BP) regulation, the lumped mathematical model of the radial artery and the PDE model of the radial artery. The inference engine is then trained using an artificial neural network technique. The training of inference engine results in the generation of a trained inference engine. In the next step, a photo-plethysmograph (PPG) signal of the person is sensed using the PPG sensor. The baseline wandering of the PPG signal is removed. Later the Fourier components of the PPG signal is extracted to generate a preprocessed PPG signal. The preprocessed PPG signal is then provided to the trained inference engine. And finally a stress parameter is generated by the inference engine based on the processed PPG signal.

In another embodiment, a non-transitory computer-readable medium having embodied thereon a computer program for estimating the stress level of the person. Initially a numerical solution to mathematical model of a blood pressure (BP) regulation is created by the processor. A numerical solution to a lumped mathematical model of a radial artery is created by the processor. A numerical solution to a partial differential equation (PDE) model of the radial artery is created by the processor. In the next step, an inference engine is generated by the processor using the mathematical model of blood pressure (BP) regulation, the lumped mathematical model of the radial artery and the PDE model of the radial artery. The inference engine is then trained using an artificial neural network technique. The training of inference engine results in the generation of a trained inference engine. In the next step, a photo-plethysmograph (PPG) signal of the person is sensed using the PPG sensor. The baseline wandering of the PPG signal is removed. Later the Fourier components of the PPG signal is extracted to generate a preprocessed PPG signal. The preprocessed PPG signal is then provided to the trained inference engine. And finally a stress parameter is generated by the inference engine based on the processed PPG signal.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and devices disclosed. In the drawings.

Figure 1:
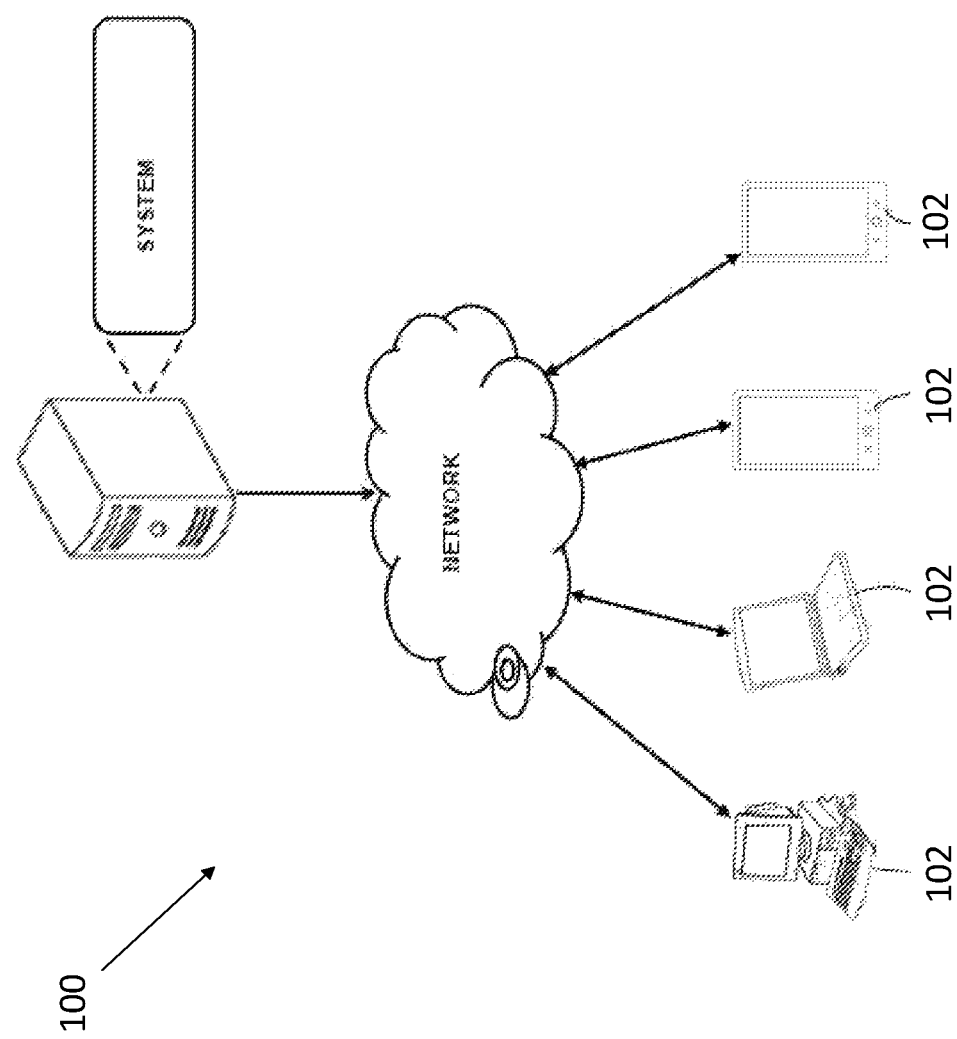
FIG. 1 illustrates a network implementation of a system for determining a stress level of a person, in accordance with an embodiment of the present disclosure.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE EMBODIMENTS

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software program executed by any hardware entity for example processor. The implementation of module as a software program may include a set of logical instructions to be executed by a processor or any other hardware entity.

The disclosed embodiments are merely exemplary of the invention, which may be embodied in various forms.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

According to an embodiment of the disclosure, a network implementation of a system 100 for determining a stress level of a person in real-time, is shown in FIG. 1. The system 100 estimates the stress parameter of a person using a differential equations based mathematical model. The differential equations based mathematical model involves variation induced by kidney, baroreceptor, fluid structure interactions of the arterial walls and blood and impedance offered by the capillaries. Further, BP regulation and stress dynamics are also taken into consideration. The mathematical model then inverted using an artificial neural network. The system 100 gives out a real number which is indicative of the stress experienced by the person.

Although the present disclosure is explained considering that the system 100 is implemented on a server, it may be understood that the system 100 may also be implemented in a variety of computing systems, such as a laptop computer, a desktop computer, a notebook, a workstation, a mainframe computer, a server, a network server, a cloud-based computing environment as shown in FIG. 1. It will be understood that the system 100 may be accessed by multiple users through one or more user devices 102-1, 102-2 ... 102-N, collectively referred to as user 102 hereinafter, or applications residing on the user devices 102. In one implementation, the system 100 may comprise the cloud-based computing environment in which a user may operate individual computing systems configured to execute remotely located applications. Examples of the user devices 102 may include, but are not limited to, a portable computer, a personal digital assistant, a handheld device, and a workstation. The user devices 102 are communicatively coupled to the system 100 through a network.

In one implementation, the network may be a wireless network, a wired network or a combination thereof. The network can be implemented as one of the different types of networks, such as intranet, local area network (LAN), wide area network (WAN), the internet, and the like. The network may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 100 may include a variety of network devices, including routers, bridges, servers, computing devices, storage devices, and the like.

Figure 2:
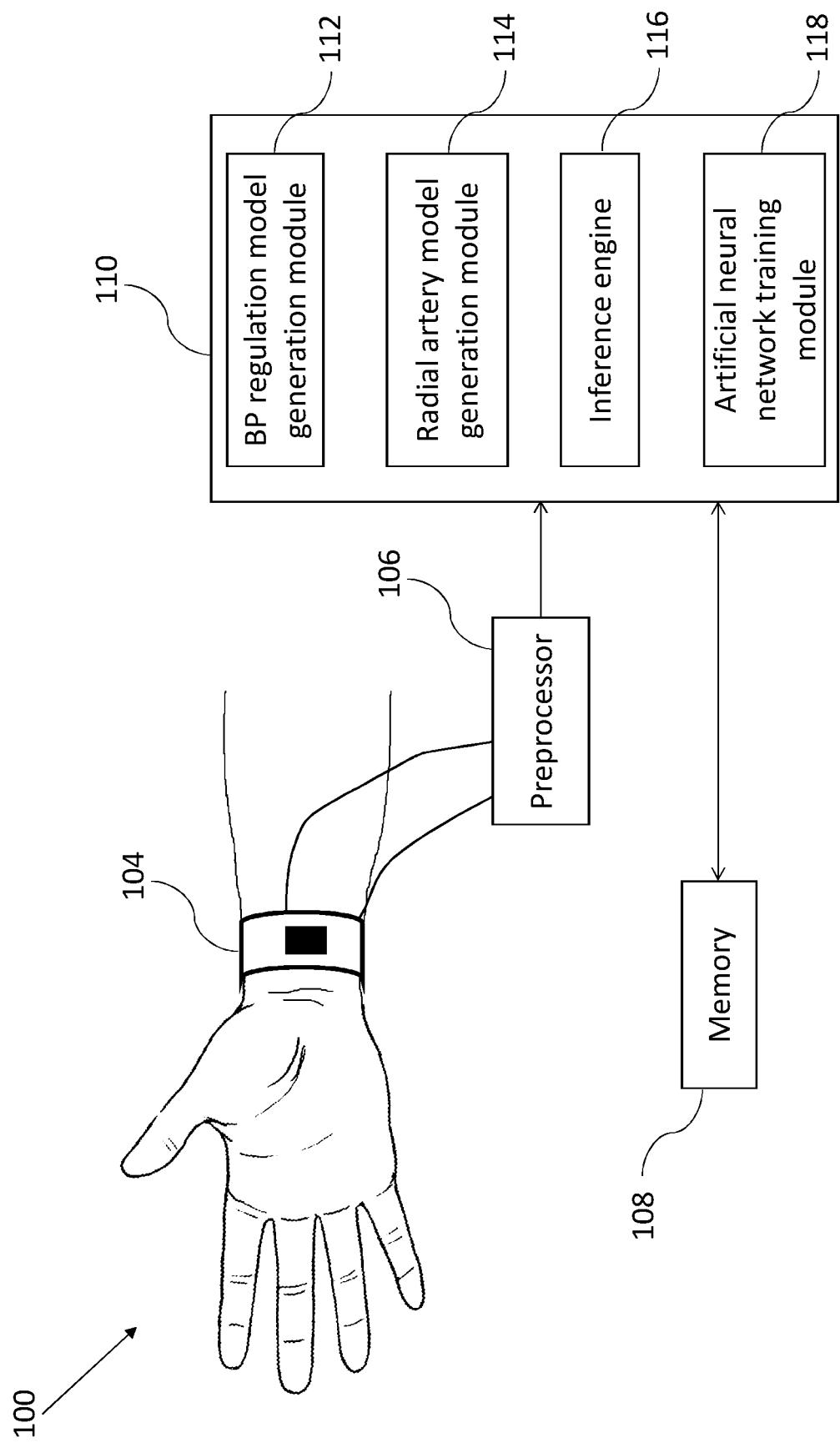
FIG. 2 illustrates a block diagram of the system for estimation of stress of the person, in accordance with an embodiment of the present disclosure.

Referring to FIG. 2, according to an embodiment of the disclosure, the system 100 comprises a photoplethysmograph (PPG) sensor 104, a preprocessor 106, a memory 108 and a processor 110. The memory 108 is in communication with the processor 110. The processor 110 further includes a plurality of modules such as a BP regulation model generation module 112, a radial artery model generation module 114, an inference engine 116 and an artificial neural network training module 118. The plurality of modules generally include routines, programs, objects, components, data structures, etc., which perform particular tasks or implement particular abstract data types. The plurality of modules described herein may be implemented as software modules that may be executed in the cloud-based computing environment of the system 100. In another embodiment the processor 110 may also include other modules performing various other functions of the system 100.

According to an embodiment of the disclosure, the processor 110 is configured to create a numerical solution to the mathematical model of the blood pressure (BP) regulation using the BP regulation model generation module 112. This model takes care of the variations induced in the signal by kidney or baroreceptors. The BP regulation involves both long term and short term regulation of blood pressure. The mathematical model of BP regulation governed by the set of equations is shown below. The governing equations in this model takes into consideration the autonomic control as well long term regulation of the blood pressure by rennin angiotensin system. It is known that a perturbation of the HPA Axis will increase the cortisol levels as it will in turn affect the autonomic nervous system firing. Here in this model it was assumed its effect gets added to the baroreflex arc parameter thus increasing the autonomic nervous system firing rate.

$$\tau_s \frac{d\bar{\varepsilon}}{dt} = \varepsilon - \bar{\varepsilon}$$

$$\frac{ds}{dt} = a(1-s) - bs\frac{\delta_\varepsilon}{\delta_\varepsilon + \delta_0}$$

$$f_{BR}(t) = f_0 s(t)\frac{\delta_\varepsilon}{\delta_\varepsilon + \delta_0}$$

$$\frac{d\phi_{SN}}{dt} = (S1 + f_{SN})(1 - \phi_{SN}) - f_{BR}\phi_{SN}$$

$$(S1 + F_{SN}) \stackrel{def}{=} F_{SN}$$

Thus $\frac{d\phi_{SN}}{dt} = F_{SN}(1 - \phi_{SN}) - f_{BR}\phi_{SN}$

Table I lists the set of parameters used in the model of autonomic nervous system.

TABLE 1

| SI # | Parameters | Explanations |
|------|------------|--------------|
| 1 | $\varepsilon$ | Strain in the aorta |
| 2 | $\bar{\varepsilon}$ | Moving average strain in aorta |
| 3 | $s$ | |
| 4 | $\bar{s}$ | |
| 5 | a | Adjustable parameters |
| 6 | b | Adjustable parameters |
| 7 | $\phi_{SN}$ | Whole body sympathetic tone |
| 8 | $f_{BR}$ | Baroreceptor firing rate |
| 9 | $f_{SN}$ | Baroreflex arc paramater |

According to an embodiment of the disclosure, the processor 110 is also configured to create a numerical solution to the mathematical model of the radial artery using the radial artery model generation module 114. The PPG waveform that is obtained from the finger also is affected by the interaction of the heart as a pump with the fluid structure interactions of the arterial system. This effect is captured using a PDE model of the radial artery. The output of this model is then used in building the inference engine. The nonlinear partial differential equations governing the flow of blood in radial artery is given below:

$$\frac{\partial A}{\partial t} + \frac{\partial (AU)}{\partial x} = 0$$

$$\frac{\partial U}{\partial t} + U\frac{\partial U}{\partial x} + \left(\frac{1}{\rho}\right)\frac{\partial P}{\partial x} = \frac{f}{\rho A}$$

Where $$P = P_{sxt} + \frac{\beta}{A_0}\left(\sqrt{A} - \sqrt{A_0}\right) + \Gamma\frac{\partial A}{\partial t}$$

$$\beta(x) = \frac{4}{3}\sqrt{\pi E h}$$

$$\Gamma(x) = \frac{\gamma}{2\sqrt{\pi A_0}}$$

The $P_{ext}=0$ as no external force is applied
Where $$\left\{A \in \Re \ \bigg| \ \frac{\partial A(0)}{\partial x} = 0, \frac{\partial A(L)}{\partial x} = 0\right\}$$

$$\left\{U \in \Re \ | \ U(0) = U(t), \frac{\partial U(L)}{\partial x} = 0\right\}$$

The function U(t) is supplied by the ODEs at one end of the artery.

A lumped parameter model of the radial artery is used to convert the output of the ODEs to velocity as experienced at one end of the artery.

$$\frac{dU(t)}{dt} = R(P_{in} - P_{out}) + \frac{R}{L}U(t)$$

The values of R and L are adjusted to suit the experimental values of radial artery area changes and velocity. $P_{in}$ is the output of the ODE system and $P_{out}$ is the capillary-pressure which again is adjusted to match the experimental observation of pressure. The equations are solved using MOL method with a spatial discretization of 64.

The outputs generated by the BP regulation model generation module 112 and the radial artery model generation module 114 is combined to generate the inference engine 116. At the same time the inference engine 116 is trained by the ANN training module 118 to generate the trained inference engine.

According to an embodiment of the disclosure, the ANN training module 118 consists of a 20 hidden layer neurons and uses ANN-LM algorithm to estimate the weights which minimizes the error (between the modelled and estimated). The set of parameters are randomly varied between ±20% of the physiological range and the corresponding pulse waveform is obtained. DFT of this waveform is then taken to extract a set of 20 real and imaginary coefficients. These coefficients with the set of parameters use in the model are then used in training the neural network to obtain the result.

In one embodiment, the photoplethysmograph (PPG) signal is captured using the PPG sensor 104. The PPG sensor 104 can be attached to the radial artery of the person. The type of the PPG sensor 104 may include, but not limited to, a piezo-electric sensor or a piezo-resistive sensor. Generally, the PPG signal captured from the PPG sensor 104 is in raw form, therefore it needs to be preprocessed before giving the signal to the trained inference engine. In an example, the PPG sensor 104 is attached to the mobile phone of the person. In another example, the PPG sensor is standalone unit.

According to an embodiment of the disclosure, the system 100 also includes the preprocessor 106. The captured PPG signal from the PPG sensor 104 is provided to the preprocessor 106. The preprocessor 106 extracts Fourier components of the PPG signal. Baseline wandering from the extracted Fourier components of the PPG signal is removed to generate a preprocessed PPG signal. The PPG signal then filtered using a Butterworth second order band pass filter. The Butterworth filter passes frequencies between 0.5-25 Hz to normalize the Fourier component of the PPG signal. This PPG signal is the normalized preprocessed PPG signal.

The preprocessed signal is then fed to the trained inference engine 116. The trained inference engine 116 then generates a stress parameter, which is indicative of the stress in the person. In an example, the stress is measured in terms of stress index $f_{SN}$. It should be appreciated that the stress parameter is measured in terms of frequency components using a measurement matrix.

Figure 3A:
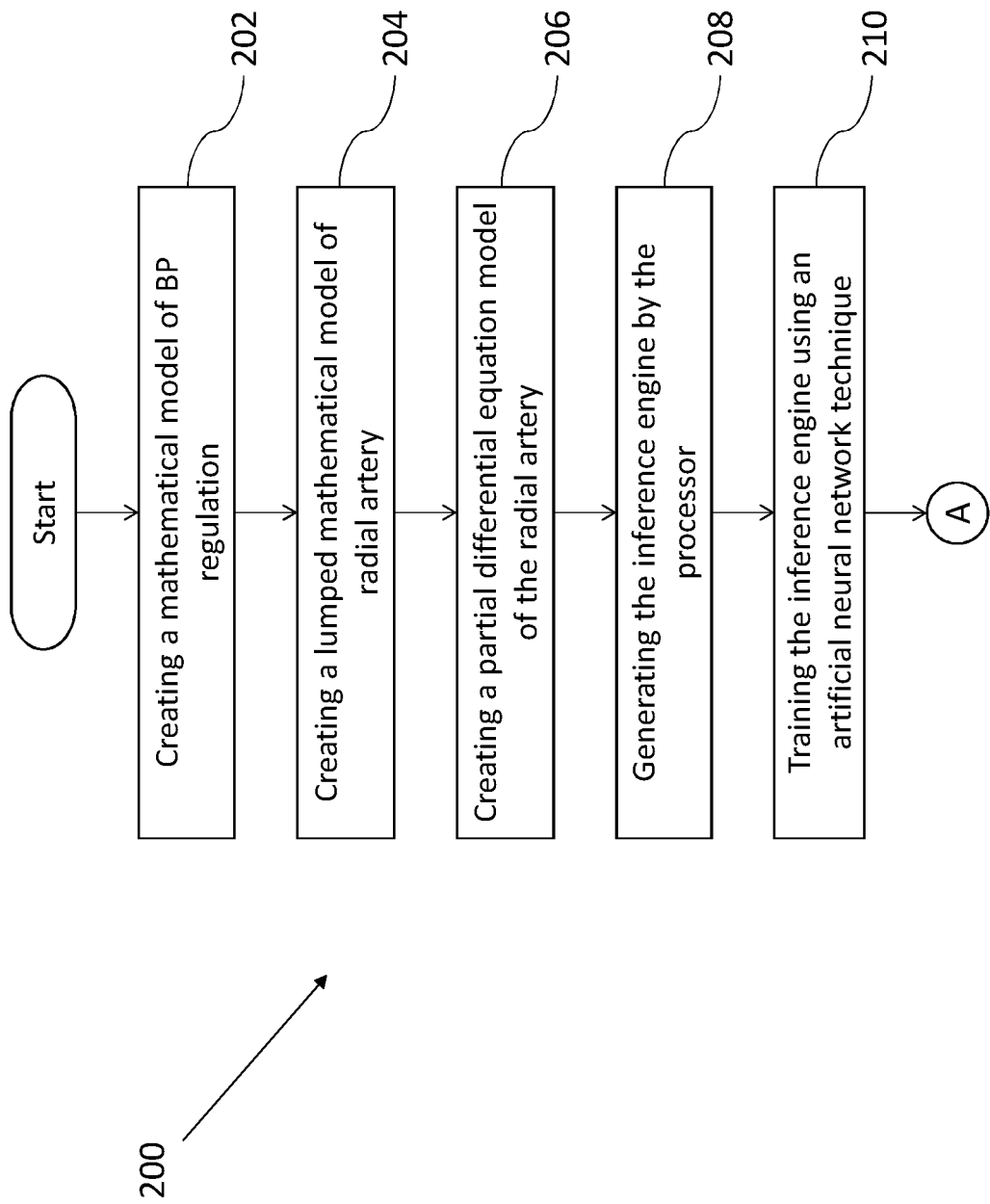
FIG. 3a-3b is a flowchart illustrating the steps involved in the estimation of stress of the person in accordance with an embodiment of the present disclosure.
Figure 3B:
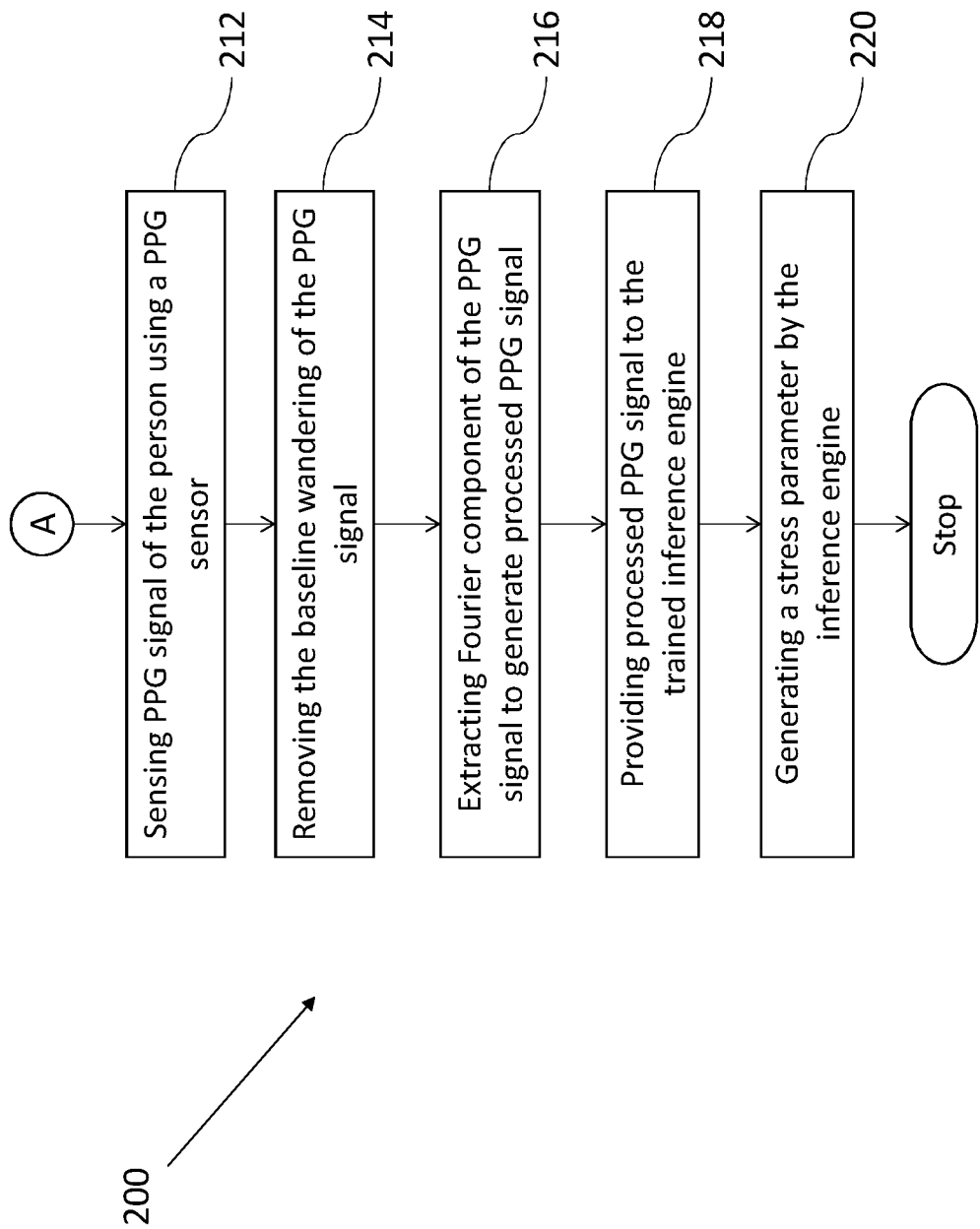

According to an embodiment of the disclosure, a flowchart 200 illustrating the steps involved in the estimation of the stress of a person is shown in FIG. 3a-3b. Initially at step 202, a numerical solution to mathematical model of the blood pressure (BP) regulation is created by the processor 110. The BP regulation takes care of the changes induced by the kidney or baroreceptors. At step 204, a numerical solution to a lumped mathematical model of a radial artery is created. And at step 206, a numerical solution to a partial differential equation (PDE) model of the radial artery is created using the processor 110. The mathematical model of the arteries thus take care of the variations that are induced by the fluid structure interactions of the artery.

In the next step 208, the inference engine 116 is generated by the processor 110 using the mathematical model of blood pressure (BP) regulation, the lumped mathematical model of the radial artery and the PDE model of the radial artery. At 210, the inference engine 116 trained by the processor 110 using an artificial neural network technique. The training results in the generation of the trained inference engine 116.

In the next step 212 a photo-plethysmograph (PPG) signal of the person is sensed using PPG sensor 104. The PPG sensor 104 can be a standalone unit or can be attached to the mobile phone of the user. The PPG signal captured from the PPG sensor 104 is then preprocessed by the preprocessor 106. At step 214, the baseline wandering of the PPG signal is removed. At step 216, the Fourier components of the PPG signal is extracted to generate the processed PPG signal. At step 218, the processed PPG signal is provided to the trained inference engine 116. And finally at step 220, a stress parameter is generated by the trained inference engine 116 based on the processed PPG signal.

According to an embodiment of the disclosure, the system 100 can also be used to compare the stress estimate between people and within the same person as the stress estimated by the system is quantitative. The comparison supports the argument that the stress is high in the mornings due to a higher sympathetic function.

According to another embodiment of the disclosure, the stress estimation method can also be personalized to take care of the individual characteristics of a person. To personalize the stress estimation a set of patient parameters are provided to the trained inference engine 116.

Figure 4:
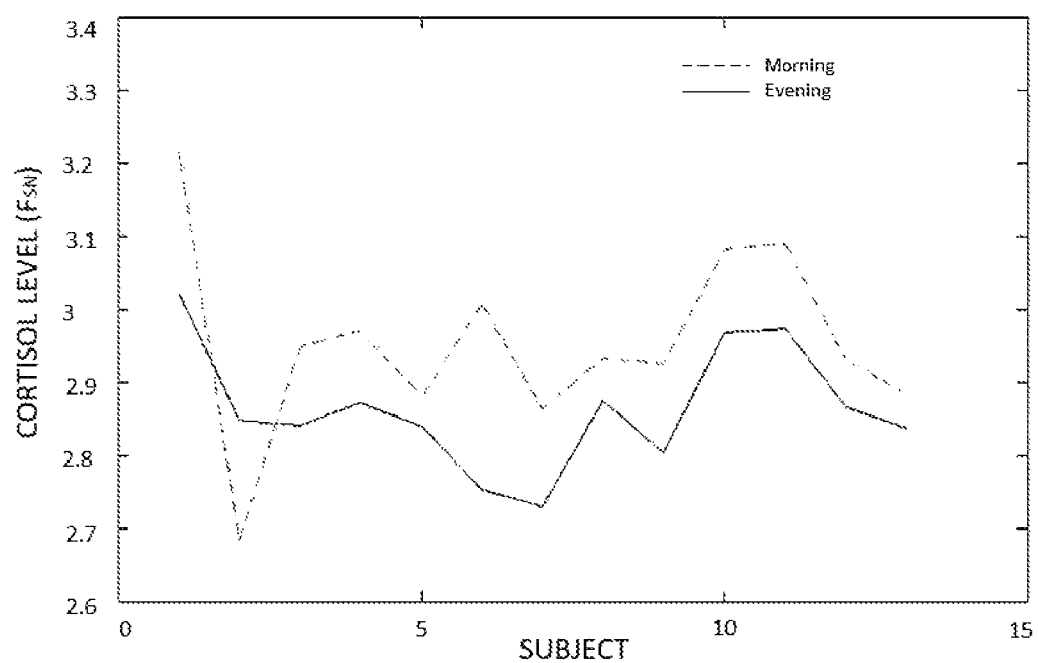
FIG. 4 shows a graphical representation of the morning and evening stress patterns in a set of individuals in accordance with an embodiment of the present disclosure.

According to another embodiment of the disclosure, the system 100 can also be used to monitor the cortisol level of the human body. The cortisol level is proportional to the stress in the human being. The graphical representation of morning and evening stress patterns in a set of individuals is shown in FIG. 4. It is known that the cortisol levels of our body follows a pattern. Its levels are known to oscillate within a day. Studies have shown that the cortisol levels are high in the mornings and low in the evenings indirectly affecting the stress in the body and thus our result of $F_{SN}$ as shown in FIG. 4.

In view of the foregoing, it will be appreciated that the present invention provides a method and system for estimation of stress using PPG signal while considering the effect of kidney, baroreceptors and radial artery blood flow. Still, it should be understood that the foregoing relates only to the exemplary embodiments of the present invention, and that numerous changes may be made thereto without departing from the spirit and scope of the invention as defined by the following claims.

What is claimed is:

1. A method for estimating stress of a person, the method comprising:

creating, by a processor, a numerical solution to a mathematical model of a blood pressure (BP) regulation, wherein the BP regulation model is based on variations induced in a photo-plethysmograph (PPG) signal by kidney or baroreceptors, wherein the BP regulation model takes baroreceptor firing rate and baroreflex arc parameter into consideration, wherein the BP regulation model includes autonomic nervous system firing rate with both long term and short term regulation of BP, wherein the autonomic nervous system firing rate is determined by monitoring a cortisol level of the person, and the determined cortisol level is added to the baroreflex arc parameter;

creating, by the processor, a numerical solution to a lumped parameter model of a radial artery, wherein the lumped parameter model is to convert an output of One-Dimensional Equations (ODEs) at one end of an artery into velocity as experienced at the one end of the artery;

creating, by the processor, a numerical solution to a partial differential equation (PDE) model of the radial artery, the PDE model corresponding to an effect of interaction of heart as a pump with fluid structure interactions of arterial system on the PPG signal;

generating, by the processor, an inference engine using the mathematical model of blood pressure (BP) regulation, the lumped parameter model of the radial artery and the PDE model of the radial artery;

training, by the processor, the inference engine using an artificial neural network technique, wherein the training results in a trained inference engine;

sensing the PPG signal of the person using a PPG sensor;

removing a baseline wandering of the PPG signal;

extracting, by the processor, Fourier components of the PPG signal to generate a preprocessed PPG signal;

providing, the preprocessed PPG signal to the trained inference engine; and generating a quantitative estimate of stress in the person by the trained inference engine based on the processed PPG signal, wherein the generated quantitative estimate of stress is a real number which is indicative of the stress experienced by the person.

2. The method of claim 1 further includes providing a set of patient parameters to the trained inference engine to personalize the stress estimation method.

3. The method of claim 1 further includes filtering the PPG signal using a Butterworth second order band pass filter which passes frequencies between 0.5-25 Hz.

4. The method of claim 1, further comprising a step of comparing the stress determined for two or more persons.

5. The method of claim 1, wherein the PPG signal is captured from the radial artery of the person.

6. The method of claim 1, wherein the PPG signal is further preprocessed to normalize the Fourier component of the PPG signal.

7. The method of claim 1, wherein the stress is measured in terms of frequency components using a measurement matrix.

8. A system for estimating a stress level of a person in real time, the system comprising:

a PPG sensor for sensing a photo-plethysmograph (PPG) signal of a person;

a preprocessor configured to preprocess the PPG signal to generate a processed PPG signal; and a memory;

a processor in communication with the memory, wherein the processor configured to perform the steps of:

creating a numerical solution to a mathematical model of a blood pressure (BP) regulation, wherein the BP regulation model is based on variations induced in a photo-plethysmograph (PPG) signal by kidney or baroreceptors, wherein the BP regulation model takes baroreceptor firing rate and baroreflex arc parameter into consideration, wherein the BP regulation model includes autonomic nervous system firing rate with both long term and short term regulation of BP, wherein the autonomic nervous system firing rate is determined by monitoring a cortisol level of the person, and the determined cortisol level is added to the baroreflex arc parameter, creating a numerical solution to a lumped parameter model of a radial artery, wherein the lumped parameter model is to convert an output of One-Dimensional Equations (ODEs) at one end of an artery into velocity as experienced at the one end of the artery, creating a numerical solution to a partial differential equation (PDE) model of the radial artery, the PDE model corresponding to an effect of interaction of heart as a pump with fluid structure interactions of arterial system on the PPG signal, generating an inference engine using the mathematical model of blood pressure (BP) regulation, the lumped parameter model of the radial artery and the PDE model of the radial artery, training the inference engine using an artificial neural network technique, wherein the training results in a trained inference engine, and generating a quantitative estimate of stress in the person by the trained inference engine based on the processed PPG signal, wherein the generated quantitative estimate of stress is a real number which is indicative of the stress experienced by the person.

9. The system of claim 8 further includes a step of preprocessing the PPG signal, wherein the preprocessing comprises:

extracting, by the preprocessor, Fourier components of the PPG signal;

filtering, by the preprocessor, the PPG signal using a Butterworth second order band pass filter which passes frequencies between 0.5-25 Hz;

removing, by the preprocessor, baseline wandering from the extracted Fourier components of the PPG signal to generate a processed PPG signal; and normalizing the Fourier component of the PPG signal.

10. The system of claim 8, wherein the PPG sensor is standalone unit or attached to a mobile phone.

11. A non-transitory computer-readable medium having embodied thereon a computer program for estimating stress of a person, the method comprising:

creating, by a processor, a numerical solution to mathematical model of a blood pressure (BP) regulation, wherein the BP regulation model is based on variations induced in a photo-plethysmograph (PPG) signal by kidney or baroreceptors, wherein the BP regulation model takes baroreceptor firing rate and baroreflex arc parameter into consideration, wherein the BP regulation model includes autonomic nervous system firing rate with both long term and short term regulation of BP, wherein the autonomic nervous system firing rate is determined by monitoring a cortisol level of the person, and the determined cortisol level is added to the baroreflex arc parameter;

creating, by the processor, a numerical solution to a lumped parameter model of a radial artery, wherein the lumped parameter model is to convert an output of One-Dimensional Equations (ODEs) at one end of an artery into velocity as experienced at the one end of the artery;

creating, by the processor, a numerical solution to a partial differential equation (PDE) model of the radial artery, the PDE model corresponding to an effect of interaction of heart as a pump with fluid structure interactions of arterial system on the PPG signal;

generating, by the processor, an inference engine using the mathematical model of blood pressure (BP) regulation, the lumped parameter model of the radial artery and the PDE model of the radial artery;

training, by the processor, the inference engine using an artificial neural network technique, wherein the training results in a trained inference engine;

sensing the PPG signal of the person using a PPG sensor;

removing a baseline wandering of the PPG signal;

extracting, by the processor, Fourier components of the PPG signal to generate a preprocessed PPG signal;

providing, the preprocessed PPG signal to the trained inference engine; and generating a quantitative estimate of stress in the person by the trained inference engine based on the processed PPG signal, wherein the generated quantitative estimate of stress is a real number which is indicative of the stress experienced by the person.

\* \* \* \* \*